United States Patent [19]

Barton

[11] Patent Number: 4,804,761

[45] Date of Patent: Feb. 14, 1989

[54] PROCESS FOR MAKING 6-ARYL-2-METHYLPYRIDINES

[75] Inventor: Alan E. Barton, Hatfield, Pa.

[73] Assignee: Rohm and Haas Company, Philadelphia, Pa.

[21] Appl. No.: 69,809

[22] Filed: Jul. 1, 1987

Related U.S. Application Data

[63] Continuation-in-part of Ser. No. 856,601, Apr. 25, 1986, abandoned.

[51] Int. Cl.$^4$ .................. C07D 213/09; C07D 213/14
[52] U.S. Cl. .................................... 546/251; 546/270; 546/348; 568/315
[58] Field of Search ...................... 546/251, 270, 348; 568/315

[56] References Cited

U.S. PATENT DOCUMENTS 4,599,421  7/1986  van der Stoel et al. ............ 546/251

FOREIGN PATENT DOCUMENTS 64750  10/1985  Switzerland ...................... 546/251

OTHER PUBLICATIONS

Chem. Abstracts 103:53935K.
Chem. Abstracts 97:162783n.
Markovac et al., J. Heterocyclic Chem., 14, 147 (1977).

Primary Examiner—Alan L. Rotman

[57] ABSTRACT

This invention relates to a process for making 6-aryl-2-methylpyridines from substituted benzaldehydes by way of 1-aryl-1,5-diketones. The 6-aryl-2-methyl-pyridines made by this process can be used in preparing biologically active 6-aryl-pyridine thiosemicarbazones.

10 Claims, No Drawings

PROCESS FOR MAKING 6-ARYL-2-METHYLPYRIDINES

BACKGROUND OF THE INVENTION

This is a continuation-in-part application of U.S. application Ser. No. 856,601 filed Apr. 25, 1986, now abandoned.

This invention relates to a process for the preparation of 6-aryl-2-methylpyridines, at times referred to herein as 6-aryl-2-picolines.

The preparation of 6-aryl-2-picolines is generally reported in the literature to be accomplished by the coupling of diazotized haloanilines with 2-picoline, Chen et al., *Heterocycles*, 5, 239 (1976); Chen et al., *Bull. Inst. Chem. Acad. Sin.*, 25, 125 (1978); the coupling of nitrophenyldiazonium hydrochloride with 2-picoline, Agarawal et al., *J. of Med. Chem.*, 17, 631 (1974); and coupling of 2-picoline with cyclohexanone in the presence of an alkyllithium reagent followed by dehydrogenation, Bonnier et al., *Bull. Soc. Chim. Fr.*, No. 4, 1204 (1967).

These literature routes produce a low yield of particular isomers which requires extensive chromatography to isolate substantially pure isomers. Further, the literature routes generally restrict the aryl group which is coupled to 2-picoline.

The present invention provides a process for making substantially isomerically homogenous 6-aryl-2-picolines in good overall yield. Further, the present invention permits a broader choice of substituents on the aryl group.

SUMMARY OF THE INVENTION

This invention relates to a process for making 6-aryl-2-picolines having the formula

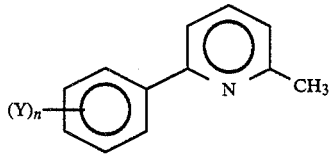

where
Y is chloro, bromo, iodo, fluoro, nitro, ($C_1$–$C_4$)alkyl, ($C_1$–$C_4$)haloalkyl, ($C_1$–$C_4$)alkoxy or ($C_1$–$C_4$)alkylthio, or when two adjacent positions on the phenyl ring are substituted with alkoxy groups, these alkoxy groups may be joined to form a dioxolano or dioxano heterocyclic ring; and
n is 0, 1, 2 or 3;
which comprises
(a) converting a 5-halo-2-pentanone derivative to the corresponding Grignard reagent or organolithium compound at a temperature of below about 100° C.; and
(b) adding a suitably substituted benzaldehyde at a temperature of from about −50° C. to about 50° C. in a suitable solvent to afford an alcohol; and
(c) subjecting the alcohol from (b) to a Jones oxidation to afford a 1-aryl-1,5-hexanedione; or treating the alcohol from (b) with manganese dioxide in a suitable solvent to afford a ketone; and
(d) reacting the 1-aryl-1,5-hexanedione or the ketone from (c) with excess hydroxylamine hydrochloride in a polar solvent at a temperature of from about 50° C. to about 100° C. to afford the 6-aryl-2-methylpyridines of Formula I.

The 6-aryl-2-methylpyridines made by this process can be used in preparing biologically active 6-arylpyridine thiosemicarbazones.

The 6-aryl-pyridine thiosemicarbazones have insecticidal activity and are capable of controlling larvae from the order Lepidoptera.

The 6-aryl-pyridine thiosemicarbazones in part affect the normal development of insects, particularly insects from the order Lepidoptera, by directly and/or indirectly influencing the moulting process.

More particularly, when 6-aryl-pyridine thiosemicarbazones are consumed by larvae, such larvae undergo a premature lethal metamorphosis. It is believed the 6-aryl-pyridine thiosemicarbazones exhibit anti-juvenile hormone activity. This activity is believed to be unique.

The 6-aryl-pyridine thiosemicarbazones are particularly suitable for controlling plant destructive insects in crops of cultivated plants, such as, but not limited to, cotton, vegetables, corn and other cereals and the like; forestry, such as but not limited to, birch, spruce, pine, fir and the like; and ornamental plants, flowers and trees. The 6-aryl-pyridine thiosemicarbazones are also particularly suitable for controlling insects destructive to stored commodities such as seeds and the like; fruit crops, such as, but not limited to, fruit and/or citrus trees, raspberry bushes and the like.

DETAILED DESCRIPTION OF THE INVENTION

This invention relates to a process for making 6-aryl-2-methylpyridines having the formula

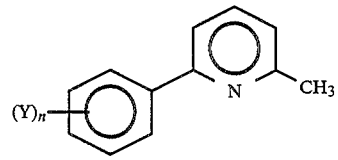

where
Y is chloro, bromo, iodo, fluoro, nitro, ($C_1$–$C_4$)alkyl, ($C_1$–$C_4$)haloalkyl, ($C_1$–$C_4$)alkoxy or ($C_1$–$C_4$)alkylthio, or when two adjacent positions on the phenyl ring are substituted with alkoxy groups, these alkoxy groups may be joined to form a dioxolano or dioxano heterocyclic ring; and
n is 0, 1, 2 or 3;
which comprises
(a) converting a 5-halo-2-pentanone derivative to the corresponding Grignard reagent or organolithium compound at a temperature of below about 100° C., preferably below about 70° C.; and
(b) adding a suitably substituted benzaldehyde at a temperature of from about −50° C. to about 50° C., preferably from about −5° C. to about 10° C., in a suitable ethereal solvent such as diethyl ether or tetrahydrofuran (THF), preferably THF, to afford an alcohol; and
(c) subjecting the alcohol from (b) to a Jones oxidation (alcohol from (b) plus $CrO_3$ in water containing sulfuric acid) to afford a 1-aryl-1,5-hexanedione; or treating the alcohol from (b) with manganese dioxide in a halogenated hydrocarbon solvent such as dichloromethane, dichloroethane, chloroform or chlorobenzene, preferably dichloromethane, to afford a ketone; and (d) reacting the 1-aryl-1,5-hexanedione or the ketone from (c) with excess hydroxylamine hydrochloride in a polar solvent such as acetonitrile, methanol, ethanol or dimethylformamide, preferably acetonitrile, at a temperature of from about 50° C. to about 100° C., preferably from about 70° C. to about 80° C. to afford the 6-aryl-2-methylpyridines of Formula I.

Schematically, the process of the present invention is shown below.

Step a:

Convert a 5-halo-2-pentanone derivative having the formula

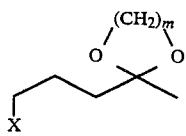

where X is halo (chloro, bromo or iodo) and m is 2 or 3; to the corresponding Grignard reagent or organolithium compound having the Formulae IIa and IIb respectively. Examples of the compounds of Formula II include 5-chloro-2-pentanone dimethyl ketal; 5-chloro-2-pentanone ethylene ketal; 5-chloro-2-pentanone propylene ketal; 5-bromo-2-pentanone dimethyl ketal; 5-bromo-2-pentanone ethylene ketal; 5-bromo-2-pentanone propylene ketal; 5-iodo-2-pentanone dimethyl ketal; 5-iodo-2-pentanone ethylene ketal; 5-iodo-2-pentanone propylene ketal.

Step b:

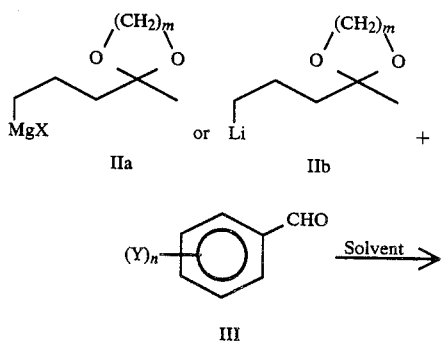

Step c:
Method 1

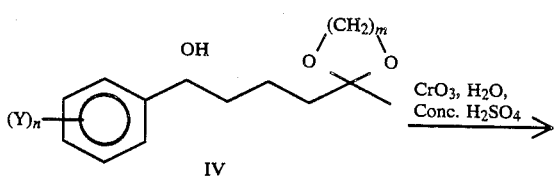

Method 2

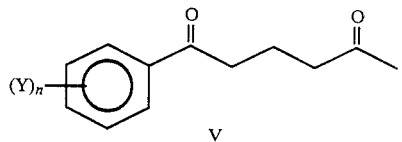

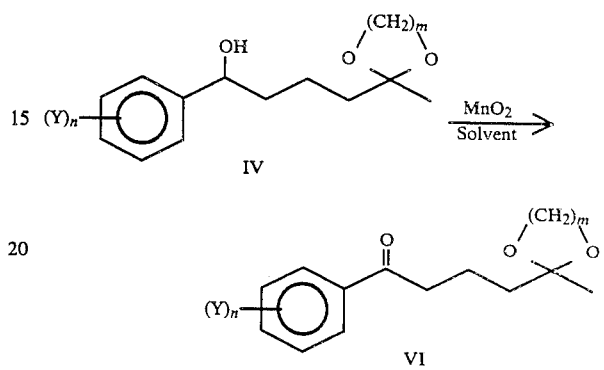

Step d:

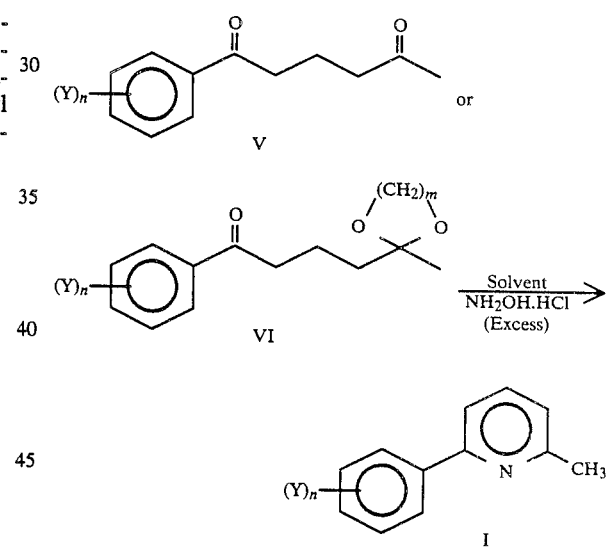

where X is halo (chloro, bromo or iodo); m is 2 or 3; and Y and n are as defined above for Formula I.

In Step a, a 5-halo-2-pentanone derivative of Formula II is converted to the corresponding Grignard reagent of Formula IIa or organolithium compound of Formula IIb at a temperature of below about 100° C., preferably below about 70° C. Procedures for preparing such a Grignard reagent or organolithium compound are known by those skilled in the art.

In Step b, the Grignard reagent or organolithium compound from Step 1 is reacted with a suitably substituted benzaldehyde of Formula III in an ethereal solvent, for example, diethyl ether or tetrahydrofuran (THF), preferably THF, at a temperature of from about −50° C. to about 50° C., preferably from about −5° C. to about 10° C. to afford the alcohol of Formula IV (a ketal of 1-hydroxy-1-aryl-5-hexanone, e.g. 1-hydroxy-1-aryl-5-dialkylketal, 1-hydroxy-1-aryl-5-dioxolano-hexanone or 1-hydroxy-1-aryl-5-dioxanohexane).

In Step c, Method 1, the alcohol of Formula IV is subjected to a Jones oxidation to afford a 1-aryl-1,5-hexanedione of Formula V; that is, to the alcohol of Formula IV, CrO₃ in water plus concentrated sulfuric acid is added to afford the 1-aryl-1,5-hexanedione of Formula V.

Alternatively, Step c, Method 2, where chromium reagents cannot be used, for example, where Y is an alkylthio group such as methylthio, the alcohol of Formula IV is treated with manganese dioxide in a suitable solvent such as halogenated hydrocarbons, for example, dichloroethane, dichloromethane, chloroform and chlorobenzene, preferably dichloromethane, to afford the ketone of Formula VI.

In Step d, the 1-aryl-1,5-hexanedione of Formula V or the ketone of Formula VI is treated with excess hydroxylamine hydrochloride in a polar solvent such as ethanol, methanol, acetonitrile and methylformamide, preferably acetonitrile, at a temperature of from about 50° C. to about 100° C., preferably from about 70° C. to about 80° C., to afford the 6-aryl-2-methylpyridine of Formula I. By "excess" hydroxylamine hydrochloride, it is meant generally from about 1.5 equivalents to about 5 equivalents, preferably from about 1.5 equivalents to about 2 equivalents of hydroxylamine hydrochloride per equivalent of the 1-aryl-1,5-hexanedione of Formula V or the ketone of Formula VI.

The compounds of Formula III and the 5-halo-2-pentanone derivatives are commercially available or can be prepared by known procedures.

Substantially equimolar amounts of reactants are preferably used in Steps a through d, except in Step d where an excess of hydroxylamine hydrochloride is employed, although higher or lower amounts can be used if desired.

Modifications to the above process may be necessary to accommodate reactive functionalities of particular matrials. Such modifications would be apparent and known to those skilled in the art.

Preferably, the process of the present invention is carried out at about atmospheric pressure, although higher or lower pressures can be used if desired.

The 6-aryl-2-methylpyridines prepared by the process of the present invention can be isolated or further reacted to prepare biologically active compounds such as certain of the 6-aryl-pyridine thiosemicarbazones disclosed in the literature references cited above and certain of the insecticidally active compounds disclosed in Le U.S. Pat. No. 4,696,938. Preparation of said biologically active thiosemicarbazones from 6-aryl-2-methylpyridines are by general synthesis routes known in the art and described in the above-cited references.

By way of example:

Step e:

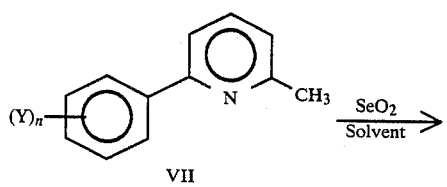

VII

Step f:
Method A

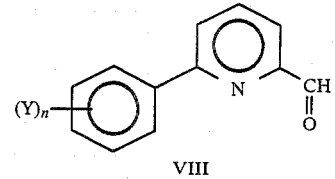

VIII

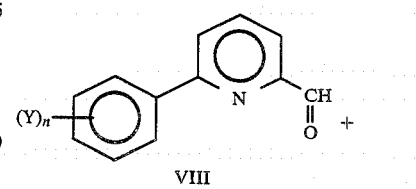

VIII

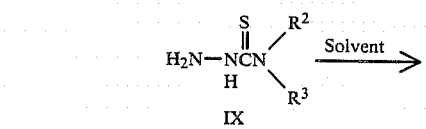

IX

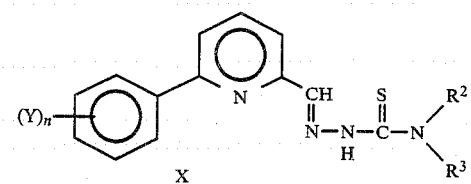

X

Method B
Stage 1:

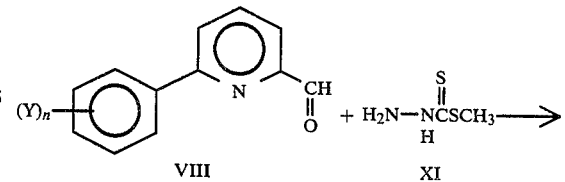

VIII    XI

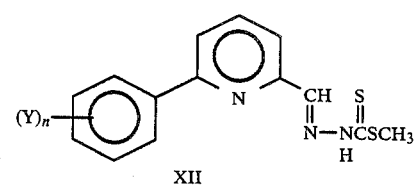

XII

Stage 2:

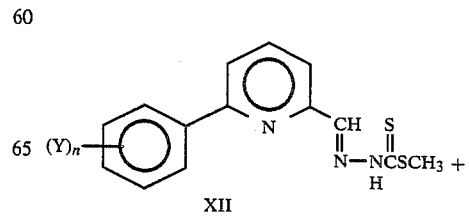

XII

-continued

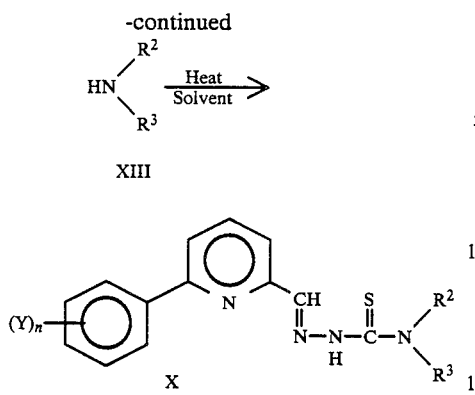

where R² and R³ are taken together with the nitrogen atom to which they are attached to form a 3 to 6 membered heterocycle having 2 to 5 nuclear carbon atoms.

In Step e, the 6-aryl-2-alkylpyridine of Formula VII is treated with selenium dioxide in a suitable ethereal solvent such as tetrahydrofuran (THF) or 1,4-dioxane, preferably 1,4-dioxane to afford the compound of Formula VIII.

In Step f, Method A, the compound of Formula VIII is reacted with the thiosemicarbazide of Formula IX in a suitable solvent such as alcohols, preferably ethanol, to afford the 6-aryl-pyridine thiosemicarbazones of Formula X.

Alternatively, Step 6, Method B, the compound of Formula VIII is reacted with a methyl hydrazinecarbodithioate of Formula XI in a suitable solvent such as alcohols, preferably isopropyl alcohol, to afford the compound of Formula XII. The compound of Formula XII is then reacted with the amine of Formula XIII in a suitable solvent, such as alcohols, preferably methanol, to afford the 6-aryl-pyridine thiosemicarbazones of Formula X.

The compounds of Formulae IX, XI and XIII are commercially available or can be prepared by known procedures.

Substantially equimolar amounts of reactants are preferably used in Steps e and f although higher or lower amounts can be used if desired.

Preferably, the above process is carried out at about atmospheric pressure, although higher or lower pressures can be used if desired.

Modifications to the above process may be necessary to accommodate reactive functionalities of particular substituents. Such modifications would be apparent and known to those skilled in the art.

The following examples are presented to further illustrate the process of this invention and are not intended to limit the breadth and scope of this invention in any way. The structure of the compound afforded by the process of the present invention was confirmed by NMR and in some cases by IR and/or elemental analysis and was either an oil or a low-melting solid. Stated yields are based on the amount of benzaldehyde used.

EXAMPLE 1

Preparation of 6-(3-bromophenyl)-2-methyl pyridine 5-chloro-2-pentanone ethylene ketal (0.0665 mol, 10 ml) was added to a suspension of magnesium (0.075 mol, 1.8 g, cleaned with ethylene dibromide) in 10 ml tetrahydrofuran (THF) so as to maintain the internal reaction temperature below 60° C. After the addition was complete, the green-gray reaction mixture was heated to about 55° C. for a further 2 hours. After cooling to about 5° C. and addition of a further 10 ml THF, a solution of 3-bromobenzaldehyde (0.05 mol, 9.2 g) in 10 ml THF was added so as to maintain the internal temperature below 10° C. After warming the mixture to room temperature, it was poured onto aqueous saturated ammonium chloride. Extraction with ether followed by drying of the extracts and evaporation of solvents afforded 18 g of a pale yellow oil.

The crude ketal-alcohol was dissolved in 200 ml of acetone, cooled to about 5° C. and treated with Jones reagent (30 ml). After the addition was complete, the heterogenous mixture was allowed to stand at room temperature for 1.5 hours. The acetone layer was decanted and the residue was extracted with ether. The combined organic extracts were washed with several portions of dilute ammonium hydroxide and then were dried. Evaporation of the solvents afforded 15 g of crude 1-aryl-1,5-hexanedione. The crude diketone was dissolved in 120 ml of acetonitrile and treated with hydroxylamine hydrochloride (0.06 mol, 4.2 g) and heated at 70°-80° C. for 16 hours. After cooling to room temperature, the mixture was partitioned between saturated aqueous sodium bicarbonate and ether. The aqueous layer was extracted with ether and the combined extracts were washed with water and dried. Evaporation of solvents yielded 6.5 g of crude pyridine which was chromatographed on silica gel using 20% ether-hexanes as eluant to give 6.0 g of 6-(3-bromophenyl)-2-methyl pyridine (49%).

EXAMPLE 2

Preparation of 6-phenyl-2-methylpyridine

The procedures of Example 1 were substantially followed except benzaldehyde was used to afford 6-phenyl-2-methylpyridine (40%).

EXAMPLE 3

Preparation of 6-(2-tolyl)-2-methylpyridine

The procedures of Example 1 were substantially followed except 2-methylbenzaldehyde was used to afford 6-(2-tolyl)-2-methylpyridine (31%).

EXAMPLE 4

Preparation of 6-(2-trifluoromethylphenyl)-2-methylpyridine

The procedures of Example 1 were substantially followed except 2-trifluoromethylbenzaldehyde was used to afford 6-(2-trifluoromethylphenyl)-2-methylpyridine.

EXAMPLE 5

Preparation of 6-(2-methoxyphenyl)-2-methylpyridine

The procedures of Example 1 were substantially followed except 2-methoxybenzaldehyde was used to afford 6-(2-methoxyphenyl)-2-methylpyridine (30%).

EXAMPLE 6

Preparation of 6-(3-nitrophenyl)-2-methylpyridine

The procedures of Example 1 were substantially followed except 3-nitrobenzaldehyde was used to afford 6-(3-nitrophenyl)-2-methylpyridine.

EXAMPLE 7

Preparation of 6-(4-bromophenyl)-2-methylpyridine

The procedures of Example 1 were substantially followed except 4-bromobenzaldehyde was used to afford 6-(4-bromophenyl)-2-methylpyridine.

EXAMPLE 8

Preparation of 6-(2-fluorophenyl)-2-methylpyridine

The procedures of Example 1 were substantially followed except 2-fluorobenzaldehyde was used to afford 6-(2-fluorophenyl)-2-methylpyridine.

EXAMPLE 9

Preparation of 6-(2-chlorophenyl)-2-methylpyridine

The procedures of Example 1 were substantially followed except 2-chlorobenzaldehyde was used to afford 6-(2-chlorophenyl)-2-methylpyridine.

EXAMPLE 10

Preparation of 6-(4-methylthiophenyl)-2-methylpyridine

The crude alcohol was prepared substantially following the procedures of Example 1 for preparing said alcohol except 4-methylthiobenzaldehyde was used.

The crude alcohol from addition of Grignard reagent to p-methylthiobenzaldehyde (7.2 g) was dissolved in 250 ml $CH_2Cl_2$. 70 g of manganese dioxide was added and the heterogeneous reaction mixture was stirred at 23° C. for about 50 hours. The entire reaction mixture was filtered through Celite and the filtrate was evaporated to give 6.3 g of ketone-ketal.

Crude ketone-ketal (4.2 g) was dissolved in approximately 50 ml acetonitrile and treated with hydroxylamine hydrochloride (2.0 g). The mixture was heated at 70°–80° C. for 6 hours. The entire reaction mixture was poured into a saturated solution of sodium bicarbonate and extracted twice with 100 ml ether. The organic extracts were washed with brine, treated with charcoal and dried over magnesium sulfate. Evaporation afforded a red/brown oil which was chromatographed on silica gel using 35% ether hexanes as eluant to give 1.55 g of 6-(4-methylthiophenyl)-2-methylpyridine as a yellow oil (50%).

EXAMPLE 11

Preparation of 6-(2,4-dichlorophenyl)-2-methylpyridine

The procedures of Example 1 were substantially followed except 2,4-dichlorobenzaldehyde was used to afford 6-(2,4-dichlorophenyl)-2-methylpyridine.

EXAMPLE 12

Preparation of 6-(2-chloro-4,5-dioxolanophenyl)-2-methylpyridine

The procedures of Example 1 were substantially followed except 2-chloro-4,5-dioxolanobenzaldehyde was used to afford 6-(2-chloro-4,5-dioxolanophenyl)-2-methylpyridine.

It is to be understood that changes and variations of this process may be made without departing from the spirit and scope of the invention as defined by the appended claims.

I claim:

1. A process for making 6-aryl-2-methylpyridines having the formula

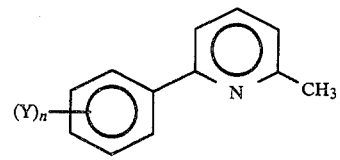

where
Y is chloro, bromo, iodo, fluoro, nitro, $(C_1-C_4)$alkyl, $(C_1-C_4)$haloalkyl, $(C_1-C_4)$alkoxy or $(C_1-C_4)$alkylthio, or when two adjacent positions on the phenyl ring are substituted with alkoxy groups, these alkoxy groups may be joined to form a dioxolano or dioxano heterocyclic ring; and n is 0, 1, 2 or 3;
which comprises
(a) treating a ketal of 1-hydroxy-1-aryl-5-hexanone with $CrO_3$ and acid to afford a 1-aryl-1,5-hexanedione; or treating the ketal of 1-hydroxy-1-aryl-5-hexanone with manganese dioxide in a suitable solvent to afford a ketone; and
(b) reacting the 1-aryl-1,5-hexanedione or the ketone from (a) with excess hydroxylamine hydrochloride in a polar solvent at a temperature of from about 50° C. to about 100° C. to afford the 6-aryl-2-methylpyridines of Formula I.

2. The process of claim 1 where in the ketal of 1-hydroxy-1-aryl-5-hexanone is prepared by converting a 5-halo-2-pentanone derivative to the corresponding Grignard reagent or organo-lithium compound at a temperature of below about 100° C.; and adding a suitably substituted benzaldehyde at a temperature of from about −50° C. to about 50° C. in a suitable solvent.

3. The process of claim 2 wherein the 5-halo-2-pentanone derivative is converted to the corresponding Grignard reagent.

4. The process of claim 3 wherein the 5-halo-2-pentanone derivative is converted to the corresponding Grignard reagent at a temperature below about 70° C.

5. The process of claim 2 wherein the benzaldehyde is added at a temperature of from about −5° C. to about 10° C.

6. The process of claim 1 wherein the ketal of 1-hydroxy-1-aryl-5-hexanone is a 1-aryl-1-hydroxy-5-dioxolano-hexane.

7. The process of claim 1 wherein the ketal of 1-hydroxy-1-aryl-5-hexanone is a 1-aryl-1-hydroxy-5-dioxano-hexane.

8. The process of claim 1 wherein (b) is carried out at a temperature of from about 70° C. to about 80° C.

9. The process of claim 1 wherein from about 1.5 equivalents to about 5 equivalents of hydroxylamine hydrochloride is used per equivalent of the 1-aryl-1,5-hexanedione or the ketone.

10. The process of claim 9 wherein from about 1.5 equivalents to about 2 equivalents of hydroxylamine hydrochloride is used.

* * * * *